(12) United States Patent
Kandapallil et al.

(10) Patent No.: US 10,401,339 B2
(45) Date of Patent: Sep. 3, 2019

(54) CLEANING COMPOSITION AND METHOD FOR ENHANCED SEALANT ADHESION

(71) Applicant: The Boeing Company, Chicago, IL (US)

(72) Inventors: Binil Itty Ipe Kandapallil, Summerville, SC (US); Carissa Ann Pajel, Mercer Island, WA (US); Dion Paul Coleman, Issaquah, WA (US); Darrin Michael Hansen, Seattle, WA (US); Judith A. Werner, Maple Valley, WA (US)

(73) Assignee: THE BOEING COMPANY, Chicago, IL (US)

( * ) Notice: Subject to any disclaimer, the term of this patent is extended or adjusted under 35 U.S.C. 154(b) by 267 days.

(21) Appl. No.: 15/459,970

(22) Filed: Mar. 15, 2017

(65) Prior Publication Data

US 2018/0265820 A1    Sep. 20, 2018

(51) Int. Cl.
| | |
|---|---|
| *G01B 11/16* | (2006.01) |
| *G01N 31/22* | (2006.01) |
| *B05D 3/10* | (2006.01) |
| *C11D 3/16* | (2006.01) |
| *C11D 3/20* | (2006.01) |
| *C11D 3/40* | (2006.01) |
| *C11D 3/43* | (2006.01) |
| *C11D 11/00* | (2006.01) |

(Continued)

(52) U.S. Cl.
CPC ............ *G01N 31/22* (2013.01); *B05D 3/102* (2013.01); *C11D 3/162* (2013.01); *C11D 3/20* (2013.01); *C11D 3/40* (2013.01); *C11D 3/43* (2013.01); *C11D 11/0023* (2013.01); *B64F 5/30* (2017.01); *B64F 5/40* (2017.01)

(58) Field of Classification Search
None
See application file for complete search history.

(56) References Cited

U.S. PATENT DOCUMENTS

| | | | |
|---|---|---|---|
| 6,605,365 | B1 | 8/2003 | Krienke et al. |
| 7,510,773 | B2 | 3/2009 | Staggs |

(Continued)

FOREIGN PATENT DOCUMENTS

EP         1828335 B1    3/2010

*Primary Examiner* — Nathan T Leong
(74) *Attorney, Agent, or Firm* — MH2 Technology Law Group LLP

(57) ABSTRACT

Methods comprising the steps of contacting a surface with a liquid composition comprising a cleaning agent, an adhesion promoter, and at least one dye, the surface having a first surface contamination; transitioning at least one portion of the surface in the first surface contamination state to a second surface contamination state and simultaneously distributing the at least one dye and at least one adhesion promoter on the surface associated with the second surface contamination state, the second surface contamination state having reduced or eliminated surface contamination, the transitioning step simultaneously cleaning and preparing the at least one portion of the surface for adhesion to another material; and identifying remaining surface in the first surface contamination state, and compositions adapted for the method thereof.

14 Claims, 5 Drawing Sheets

(51) Int. Cl.
 *B64F 5/30* (2017.01)
 *B64F 5/40* (2017.01)

(56) References Cited

U.S. PATENT DOCUMENTS

| | | | |
|---|---|---|---|
| 8,697,179 B2* | 4/2014 | Osborne | C09D 5/002 |
| | | | 106/287.19 |
| 8,720,278 B1* | 5/2014 | Toivola | G01B 11/16 |
| | | | 73/762 |
| 9,085,052 B1 | 7/2015 | Georgeson et al. | |
| 2009/0208758 A1 | 8/2009 | D'Herbecourt et al. | |
| 2015/0044381 A1 | 2/2015 | Park et al. | |
| 2016/0228685 A1 | 8/2016 | Pugh et al. | |

* cited by examiner

CLEANING COMPOSITION AND METHOD FOR ENHANCED SEALANT ADHESION

TECHNICAL FIELD

The present disclosure relates to methods of cleaning/activating a surface before application of sealant, comprising contacting the substrate with an adhesion promoter in combination with a cleaning agent and a dye enabling visual inspection of the surface prior to application of the sealant.

BACKGROUND

Different applications of sealants include solvent-proofing, thermal and acoustic insulation, electrical and electromagnetic insulation, fire-barrier protection or even providing aesthetic appeal to structures for a variety of industries. The types of sealant functionality depends on chemical and physical characteristics of the sealant and substrate surface.

In the event of a sealant adhesion failure, the sealant fails to establish strong physical/chemical bond with the substrate due to the presence of contaminants that spoils the sealant or inhibits chemical/physical bond formation with the substrate. In order to ensure proper sealant adhesion, the substrate needs to be cleaned/modified/activated to facilitate adhesive interactions for which surface preparation is an important step.

Cleaning the substrate with a suitable solvent is the first line of defense to prevent sealant adhesion failure. Although the solvent of choice should depend on the solvation capability of a solvent for the prevalent contamination type for effective cleanability, the actual solvent used depends on various health and safety requirements and regulations for a particular application. Hence it would be desirable to develop a surface cleaning technology that would impart sufficient adhesion strength for the sealant material even in the presence of nominal quantities of contaminants. Moreover, it is further desirable to have an inspection capability to quantify or qualify that cleaning has been attempted and achieved to a desired level with the specific solvent. Although adhesion promoters are commercially available, there are limitations for its use, more particularly, it is applied on the surface as an additional step after the cleaning stage has been accomplished. Additionally, commercially available adhesion promoters necessitate subsequent additional process steps or requires activation and/or certain facilities requirements.

SUMMARY

In a first example, a method of improving adhesion of sealant to a surface is provided, the method comprising the steps of: (i) contacting a surface with a liquid composition comprising at least one cleaning agent, at least one adhesion promoter, and at least one dye; (ii) transitioning at least one portion of the surface in a first surface contamination state to a second surface contamination state and simultaneously distributing the at least one dye on the surface associated with the second surface contamination state, the second surface contamination state having reduced or eliminated surface contamination, the transitioning step simultaneously cleaning and preparing the at least one portion of the surface for adhesion to or by another material; (iii) identifying remaining surface in the first surface contamination state after steps (i) and (ii) by the visual distribution of the at least one dye on the surface.

In one aspect, the method further comprising repeating steps (i) and (ii) after step (iii).

In one aspect, alone or in combination with any of the previous aspects, the at least one cleaning agent comprises at least one volatile organic solvent. In another aspect, alone or in combination with any one of the previous aspects, the at least one volatile organic solvent is selected from the group consisting of Methyl Ethyl Ketone (MEK), Methyl n-Propyl Ketone (MPK), Toluene, Isopropyl Alcohol (IPA), and Methyl Isobutyl Ketone (MIBK), acetone, and a mixture of: monopropylene glycol methyl ether, 2-methoxy 1-methylethyl acetate, and $C_{9-11}$ n-alkanes, isoalkanes, cyclics with less than 2 weight percent aromatics.

In one aspect, alone or in combination with any one of the previous aspects, the at least one adhesion promoter includes one or more of a transition metal alkoxide or a metal alkylalkoxide. In another aspect, alone or in combination with any one of the previous aspects, the transition metal alkoxide or the metal alkylalkoxide is selected from mono-, di-, tri- and tetra (alkyl)alkoxides of aluminum, titanium, and zirconium. In another aspect, alone or in combination with any one of the previous aspects, the transition metal alkoxide or the metal alkylalkoxide is selected from the group consisting of zirconium(IV) bis(diethyl citrato) dipropoxide; titanium(IV) (triethanolaminato)isopropoxide; titanium bis(triethanolamine)diisopropoxide; titanium(IV) butoxide polymer; titanium(IV) butoxide; titanium(IV) oxyacetylacetonate; titanium(IV) bis(ammonium lactato)dihydroxide; oxobis(2,2,6,6-tetramethyl-3,5-heptanedionato)titanium(IV); titanium(IV) diisopropoxidebis(2,2,6,6-tetramethyl-3,5-heptanedionate); titanium diisopropoxide bis(acetylacetonate); titanium(IV) tert-butoxide; titanium tetrakis(2-ethylhexanoate); titanium tetraisopropoxide; titanium tetrabutanoxide; and titanium (IV) 2-ethylhexanoate.

In one aspect, alone or in combination with any one of the previous aspects, the at least one adhesion promoter includes one or more of an epoxy-, or mercapto-functionalized mono-, di-, or tri-(alkyl)alkoxyl siloxane. In another aspect, alone or in combination with any one of the previous aspects, the siloxane is selected from the group consisting of (3-aminopropyl)triethoxysilane; (gamma-mercaptopropyl)trimethoxysilane; 3-glycidoxypropyltrimethoxysilane; 3-mercapto propyltrimethoxysilane; and isocyanatopropyltriethoxysilane (IPS).

In one aspect, alone or in combination with any one of the previous aspects, the at least one dye has at least one absorption maximum between 390 nanometers and 700 nanometers. In another aspect, alone or in combination with any one of the previous aspects, the at least one dye is selected from the group consisting of Fluorescein (3',6'-dihydroxyspiro[isobenzofuran-1(3H),9'-[9H]xanthen]-3-one); Rose Bengal (4,5,6,7-tetrachloro-3',6'-dihydroxy-2',4',5',7'-tetraiodo-3H-spiro[isobenzofuran-1,9'-xanthen]-3-one); Erythrosine B (2-(6-hydroxy-2,4,5,7-tetraiodo-3-oxoxanthen-9-yl)benzoic acid); Allura Red (disodium 6-hydroxy-5-[(2-methoxy-5-methyl-4-sulfophenyl)azo]-2-naphthalenesulfonate); Indigotine (a mixture of disodium 3,3'-dioxo-[delta2,2'-biindoline]-5,5'-disulfonate, and disodium 3,3'-dioxo-[delta2,2'-biindoline]-5,7'-disulfonate); Fast Green (ethyl-[4-[[4-[ethyl-[(3-sulfophenyl)methyl]amino]phenyl]-(4-hydroxy-2-sulfophenyl)methylidene]-1-cyclohexa-2,5-dienylidene]-[(3-sulfophenyl)methyl]azanium); Basic Blue 41 ([[4-[ethyl(2-hydroxyethyl)amino]phenyl]azo]-6-methoxy-3-methylbenzothiazoliummethylsulphate); Direct Red 81 (disodium 7-benzamido-4-hydroxy-3-[[4-[(4-sulphonatophenyl)azo]phenyl]azo]naphthalene-2-sulphonate); and Methylene Blue (3,7-bis(dimethylamino)phenazathionium chloride.

In one aspect, alone or in combination with any one of the previous aspects, the surface is metal, metal alloy, or a metal or metal alloy surface previously coated with a sealant coating. In another aspect, alone or in combination with any one of the previous aspects, the method further comprises contacting the metal or the metal alloy surface with a sealant. In another aspect, alone or in combination with any one of the previous aspects, the method further comprises contacting the metal or the metal alloy surface previously coated with a sealant coating with the same sealant or a different sealant.

In a second example, a dyed solvent composition is provided; the wipe solvent composition comprising: an environmentally acceptable volatile organic solvent or mixture thereof; at least one dye having an absorption maximum between 390 nanometers and 700 nanometers and at least one adhesion promoter having: a bonding affinity for a metal substrate surface cleanable by the environmentally acceptable volatile organic solvent or mixture; and a bonding affinity for a sealant subsequently applied to the metal surface. In one aspect, the at least one dye is present in an amount between about 0.001 to about 0.1 weight percent of the dyed composition. In one aspect, alone or in combination with any one of the previous aspects, the at least one adhesion promoter is present in an amount between about 0.01 to about 2.0 volume percent of the dyed composition. In one aspect, the composition is devoid of surfactant.

In another aspect, alone or in combination with any one of the previous aspects, the environmentally acceptable volatile organic solvent or mixture thereof is selected from the group consisting of Methyl Ethyl Ketone (MEK), Methyl n-Propyl Ketone (MPK), Toluene, Isopropyl Alcohol (IPA), and Methyl Isobutyl Ketone (MIBK), acetone, and a mixture of: monopropylene glycol methyl ether, 2-methoxy 1-methylethyl acetate, and $C_{9-11}$ n-alkanes, isoalkanes, and cyclics with less than 2 weight percent aromatics.

In another aspect, alone or in combination with any one of the previous aspects, the at least one adhesion promoter is selected from the group consisting of zirconium(IV) bis(diethyl citrato)dipropoxide; titanium(IV) (triethanolaminato)isopropoxide; titanium bis(triethanolamine)diisopropoxide; titanium(IV) butoxide polymer; titanium(IV) butoxide; titanium(IV) oxyacetylacetonate; titanium(IV) bis (ammonium lactato)dihydroxide; oxobis(2,2,6,6-tetramethyl-3,5-heptanedionato)titanium(IV); titanium(IV) diisopropoxidebis(2,2,6,6-tetramethyl-3,5-heptanedionate); titanium diisopropoxide bis(acetylacetonate); titanium(IV) tert-butoxide; titanium (IV) 2-ethylhexanoate; (3-aminopropyl)triethoxysilane; (gamma-mercaptopropyl)trimethoxysilane; 3-glycidoxypropyltrimethoxysilane; 3-mercapto propyltrimethoxysilane; and isocyanatopropyltriethoxysilane (IPS).

In another aspect, alone or in combination with any one of the previous aspects, the at least one dye is selected from the group consisting of Fluorescein (3',6'-dihydroxyspiro [isobenzofuran-1(3H),9'-[9H]xanthen]-3-one); Rose Bengal (4,5,6,7-tetrachloro-3',6'-dihydroxy-2',4',5',7'-tetraiodo-3H-spiro[isobenzofuran-1,9'-xanthen]-3-one); Erythrosine B (2-(6-hydroxy-2,4,5,7-tetraiodo-3-oxo-xanthen-9-yl)benzoic acid); Allura Red (disodium 6-hydroxy-5-[(2-methoxy-5-methyl-4-sulfophenyl)azo]-2-naphthalenesulfonate); Indigotine (a mixture of disodium 3,3'-dioxo-[delta2,2'-biindoline]-5,5'-disulfonate, and disodium 3,3'-dioxo-[delta2, 2'-biindoline]-5,7'-disulfonate); Fast Green (ethyl-[4-[[4-[ethyl-[(3-sulfophenyl)methyl]amino]phenyl]-(4-hydroxy-2-sulfophenyl)methylidene]-1-cyclohexa-2,5-dienylidene]-[(3-sulfophenyl)methyl]azanium); Basic Blue 41 ([[4-[ethyl (2-hydroxyethyl)amino]phenyl]azo]-6-methoxy-3-methylbenzothiazoliummethylsulphate); Direct Red 81 (disodium 7-benzamido-4-hydroxy-3-[[4-[(4-sulphonatophenyl)azo]phenyl]azo]naphthalene-2-sulphonate); and Methylene Blue (3,7-bis(dimethylamino)phenazathionium chloride.

BRIEF DESCRIPTION OF THE DRAWINGS

Preferred and alternate examples of the present disclosure are described in detail below with reference to the following drawings.

DETAILED DESCRIPTION

Figure 1:
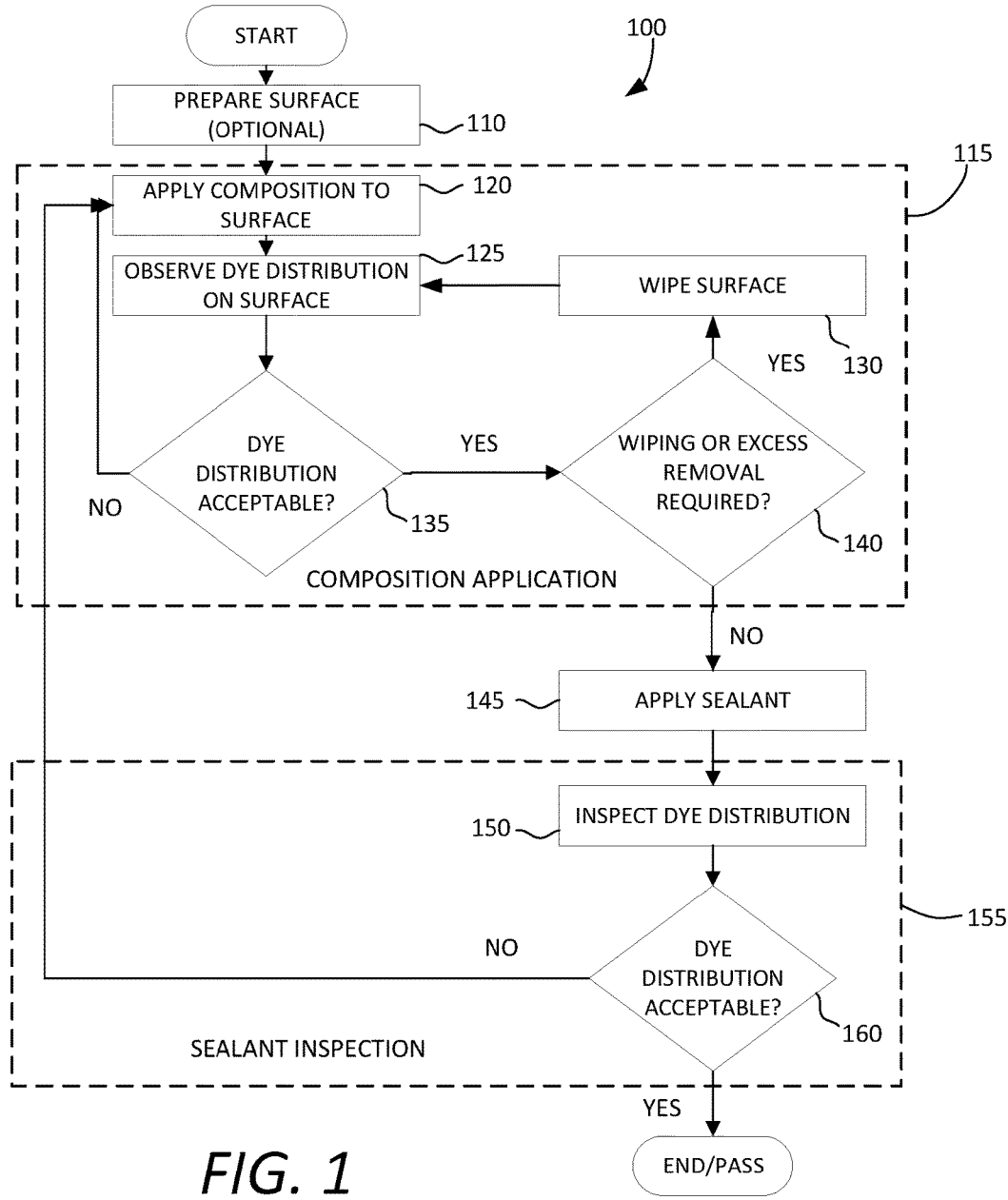
FIG. 1 is a is a flow diagram illustrating steps that are followed in accordance with an example of the present disclosure.

Conventional methods of sealing an aircraft in a manufacturing environment include cleaning with solvent, application of adhesion promoter, inspection of cleaned area and application of sealant. In some instances, use of adhesion promoter is not utilized. In instances where adhesion promoter is utilized, commercially available adhesion promoters necessitates subsequent process, e.g., hydrolysis of the adhesion promoter, for activation. Moreover, in some instances, it is difficult to determine if an area has been cleaned thoroughly prior to sealant application or adhesion promotion processes. Insufficiently cleaned areas will cause adhesion failure of the sealant resulting in the need for rework, including repeating the entire process all over again. Also, some conventional methods of cleaning and/or adhesion promotion are not conducive to confined-space or low-light/low-ventilated environments, for example, for health and safety reasons.

The subject matter of the present application provides a technical solution in response to needs associated with methods of sealing an aircraft surface as referenced herein and in the accompanying drawings that overcome at least some of the abovementioned shortcomings of having separate cleaning/adhesion processes, which can result in increased manufacturing cost and time. As an example, in some embodiments, methods described herein provide for the cleaning, treatment and reactivation of an aircraft surface in a one-step process that further allows inspection and a process suitable for a confined-space and/or low-light/low-ventilated environment.

The present disclosure relates a one-step cleaning, treating and reactivating process preceding sealant application. The method is suitable, for example, for preceding a sealant application to an aircraft surface, such as bare aluminum, coated aluminum, or carbon fiber composite panel substrate. This present disclosure is more specifically directed to methods of a one-step cleaning, treating and reactivating an aircraft surface with the present composition comprising at least a solvent or at least a mixture of solvents, at least an adhesion promoter, and with at least one dye as a visual inspection indicator.

Examples of the present disclosure may provide an effective solution to increased production with reduced labor, including cost and time, associated with preparing various treated surfaces for the application of a fresh material to the surface. Furthermore, examples of the present disclosure provide a single-step method of simultaneously cleaning and promoting adhesion that eliminates a separate processing step while providing for visual inspection of the surface. The present disclosure also eliminates or reduces the need for using scuff sanding and other mechanical layer removal methods. Examples of the present disclosure are useful in the aerospace industry and any other industry where surface preparation and adhesion are important.

In one example, a substrate surface is contacted with the present composition comprising one or more volatile organic compounds, one or more dyes providing a color discernible to the human eye, and a suitable adhesion promoter. The present composition may also include co-solvents, and other desired ingredients as necessary to promote cleaning and subsequent adhesion to the surface.

Upon combining the cleaning agent, dye, adhesion promoter, and other desired ingredients to form the present composition, the solution is applied to the substrate, herein referred to as the treated surface, is simultaneously cleaned and adhesion-activated. Here, adhesion-activate means that the substrate is brought to a condition whereby adhesion between the substrate and a second material is promoted, improved, or enhanced ("bonding affinity") as compared to the same surface without such treatment.

In one example, a composition for use as a cleaning composition is provided, the solution comprising: one or more solvents; one or more adhesion promoters; and one or more dyes. In one aspect, the one or more solvents constitute approximately 99 weight percent of the composition, the one or more adhesion promoters constitutes less than 10 volume percent, less than 7 volume percent, less than 5 volume percent, or less than 2 volume percent of the composition; and the one or more dyes constitute 0.01-0.05 weight percent of the composition. Other weight percentages may be used. Advantageously, the weight percent of adhesion promoter is much less than that commercially available (usually around 10 volume percent) and provides for mixing with a variety of organic solvents and/or cleaning agents useful in the practice of the present disclosure. The low weight percent of adhesion promoter in such organic solvents and/or cleaning agents reduces or eliminates precipitation of the adhesion promoter, improves storage stability, and reduces cost.

In one aspect, the one or more dyes are present at about 0.001 to 0.1 weight percent of the composition, or from about 0.01 to 0.05 weight percent depending in part on the absorption coefficient, molecular weight, and solubility of the particular dye. Advantageously, the weight percent of dye is chosen so that it is visible to the human eye on a surface under confined space or lowlight environment application conditions of the present composition, for example. Such conditions include essentially complete volatilization of the cleaning agent from the surface or the removal of the cleaning agent by physical means, e.g., wiping.

In one example, a composition for use as a cleaning composition is provided, the solution comprising: one or more solvents; one or more adhesion promoters; and one or more dyes. In one aspect, the one or more solvents constitute approximately 99 weight percent, the one or more adhesion promoters constitutes about 0.1-1.0 volume percent; and the one or more dyes constitute 0.01-0.05 weight percent of the composition. Other weight percentages may be used.

The present composition in accordance with examples of the present disclosure may advantageously include a mixture of at least one cleaning agent, at least one dye, and at least one adhesion promoter. In one aspect, the cleaning agent is a solvent capable of dissolving contaminates generally known to be present on such surfaces in need of sealant application. In one aspect, the solvent is one or more organic compounds. In particular examples, the present composition includes as the cleaning agent, one or a chemical blend of volatile organic solvents, including but not limited to, Methyl Ethyl Ketone (MEK), Methyl n-Propyl Ketone (MPK), Toluene, Isopropyl Alcohol (IPA), and Methyl Isobutyl Ketone (MIBK), acetone, dyeSTONE DLS (a mixture of monopropylene glycol methyl ether, 2-methoxy 1-methylethyl acetate, and $C_{9-11}$ n-alkanes, isoalkanes, and cyclics with <2% aromatics) and a suitable adhesion promoter. In one particular example, the four organic solvents listed above for the present composition may currently be found in DESOCLEAN® 45 commercially available from PRCDeSoto International, Inc. of Glendale, Calif. The vapor pressure of the present composition may be below about 45 mm Hg so as to meet environmental standards. Additional solvents, such as Oxol 100®, also known as parachlorobenzotrifluoride, may be added to the cleaning agent, as necessary, to assist in the solubility of the promoter. Other solvents and co-solvents may be used.

The volume ratio organic solvents used may be adjusted so as to meet the vapor pressure standards and to achieve solubility of the adhesion promoter. The adhesion promoter is configured to interact with hydroxyl groups present on the surface of the substrate and/or to provide an interface between the surface and the sealant to effect an improved adhesion thereof. In some examples, the adhesion promoter comprises one or more hydrolyzable groups chemically bound to a transition metal or non-metal capable of reacting with the hydroxyl groups present on the surface of the substrate. In some examples, the adhesion promoter comprises one or more hydrolyzable groups and at least one non-hydrolyzable group chemically bound to a transition metal or non-metal, the hydrolyzable groups capable of reacting with the hydroxyl groups present on the surface of the substrate.

In one aspect, the one or more adhesion promoters include transition metal alkoxides, transition metal alkylalkoxides, epoxy-, or mercapto-functionalized mono-, di-, and tri-(alkyl)alkoxyl siloxanes. Examples of transition metal alkoxides and alkylalkoxides include mono-, di-, tri- and tetra (alkyl)alkoxides of aluminum, titanium, and zirconium. Examples of transition metal alkoxides and alkylalkoxides also include functionalized derivatives such as zirconium (IV) bis(diethyl citrato)dipropoxide; titanium(IV) (triethanolaminato)isopropoxide; titanium bis(triethanolamine)diisopropoxide; titanium(IV) butoxide polymer; titanium(IV) oxyacetylacetonate; titanium(IV) bis(ammonium lactato)dihydroxide; oxobis(2,2,6,6-tetramethyl-3,5-heptanedionato) titanium(IV); titanium(IV) diisopropoxidebis(2,2,6,6-tetramethyl-3,5-heptanedionate); titanium diisopropoxide bis (acetylacetonate); titanium(IV) tert-butoxide; and titanium (IV) 2-ethylhexanoate.

Examples of functionalized siloxanes include (3-aminopropyl)triethoxysilane; (gamma-mercaptopropyl)trimethoxysilane; 3-glycidoxypropyltrimethoxysilane; 3-mercapto propyltrimethoxysilane; isocyanatopropyltriethoxysilane (IPS) and the like, and include polymeric variants of these compounds.

In one aspect, suitable dyes include those that remain on the surface of the substrate and are visually observable under visible light conditions such as white light. Particular examples of suitable dyes that are visible under white light include: Fluorescein (3',6'-dihydroxyspiro[isobenzofuran-1 (3H),9'-[9H]xanthen]-3-one); Rose Bengal (4,5,6,7-tetrachloro-3',6'-dihydroxy-2',4',5',7'-tetraiodo-3H-spiro[isobenzofuran-1,9'-xanthen]-3-one); Erythrosine B (2-(6-hydroxy-2,4,5,7-tetraiodo-3-oxo-xanthen-9-yl)benzoic acid); Allura Red (disodium 6-hydroxy-5-[(2-methoxy-5-methyl-4-sulfophenyl)azo]-2-naphthalenesulfonate); Indigotine (consisting essentially of a mixture of disodium 3,3'-dioxo-[delta2,2'-biindoline]-5,5'-disulfonate, and disodium 3,3'-dioxo-[delta2,2'-biindoline]-5,7'-disulfonate); or Fast Green (ethyl-[4-[[4-[ethyl-[(3-sulfophenyl)methyl]amino]phenyl]-(4-hydroxy-2-sulfophenyl)methylidene]-1-cyclohexa-2,5-dienylidene]-[(3-sulfophenyl)methyl]azanium). Basic Blue 41 ([[4-[ethyl(2-hydroxyethyl)amino]phenyl]azo]-6-methoxy-3-methylbenzothiazoliummethylsulphate); Direct Red 81 (disodium 7-benzamido-4-hydroxy-3-[[4-[(4-sulphonatophenyl)azo]phenyl]azo]naphthalene-2-sulphonate); Methylene Blue (3,7-bis(Dimethylamino)phenazathionium chloride); and the like. In another aspect, suitable dyes include those that are visually observable under UV or infrared light. Particular examples of suitable dyes visible under ultraviolet (UV) light include: Pyranine dye (trisodium 8-hydroxypyrene-1,3,6-trisulfonate); Basic Red 1 (rhodamine 6G); L-142; L-174; L-182; L-187; L-212; and the like. These and other suitable dyes that are visible under white light and/or UV light are available at: Sigma-Aldrich, Milwaukee, Wis., USA; VWR Scientific Products, West Chester, Pa., USA; Keystone Aniline Corporation, Chicago, Ill., USA; and Beaver Luminescers, Newton, Mass., USA. Dyes having an optical behavior that changes as a function of a stress, thickness, or pH/oxidation of the sealant may be used. For example, the dye can be a mechanochromatic dye such as a functionalized stilbene dye having one of tert-butyl dimethylsilane end groups or hydroxyl end groups, or pH dependent as to its color. Other dyes may be used, in particular, ones that are visible to the human eye (an absorption maxima in the visible spectrum of light).

In another aspect, the dye includes a visual moiety chemically tethered or bound via hydrogen bonds, covalent bonds and the like, to a constituent of the surface of the substrate or the adhesion promoter. For example, by reacting hydroxyl or amine terminated dye compounds with an isocyanate terminated alkoxysilane, the dye may be substantially immobilized to the adhesion promoter and/or the surface of the substrate. It is an advantage of this example that the tendency of the dye to migrate from the surface of the substrate is reduced or eliminated. In one aspect, relatively large and/or insoluble dye molecules may be used or tethered to relatively large and/or insoluble moieties so as to substantially prevent the dye from migrating from or washing away from the surface of the substrate. By way of example, a material that features a visible moiety attached to a silicon alkoxide group can be used.

Previous solutions to the problem of preparing a substrate surface to receive a sealant with good adhesion included cleaning a substrate surface with a solvent followed by a separate or distinct application of an adhesion promoter. Application of commercially available adhesion promoter formulations are typically regulated by Environmental Health and Safety (EHS) depending on specific application locations (e.g., confined space). Application of adhesion promoter is an added step after the general cleaning step. The new solution combines what would typically be a two-step process, into a one step process wherein the solvent, dye, and the adhesion promoter are combined into a single cleaning formulation. A regular adhesion promotion process may or may not be applied after the present cleaning composition has been applied. In one aspect, the present method comprises applying the present composition multiple times and providing an effective layer of adhesion promoter and dye left behind on the substrate.

The present disclosure relates to methods of applying a cleaning agent with an adhesion promoter and at least one dye to form a present composition. Many specific details of certain examples of the present disclosure are set forth in the following description and in the figures to provide an understanding of the presently disclosed methods. One skilled in the art, however, will understand that the present disclosure may have additional examples, or that the present disclosure may be practiced without several of the details described in the following description. The present disclosures provides a technical solution to the above problem of providing a suitable substrate surface for subsequent sealant application while also providing the improvement of preventing or eliminating sealant adhesion failure from the substrate.

Some of the major chemical classes of sealants are polysulfides, polythioethers, polysilicones, polysiloxanes, epoxides, and polyurethanes. In one aspect, the sealant includes two-part polysulfide manganese-based sealants.

In general, examples of methods in accordance with the present disclosure provide an efficient and cost-effective solution to production and labor issues associated with preparing various substrate surfaces for adhesion between the substrate and a second material. Because examples of the present disclosure are adapted to handle a wide variety of substrate surfaces, multiple applications may be suitable.

FIG. 1 is a flow diagram of a method 100 according to an example of the present disclosure. In general, the method 100 includes an optional surface preparation step 110, composition application step 120, dye distribution evaluation step 125, and an optional composition application repeat step 135.

The surface 202 of a substrate is optionally prepared for contact with the presently disclosed composition at step 110. If performed, the surfacing preparation may include one or more of abrading, acid etching, and the like. Depending upon the various manufacturing procedures performed to generate the surface, preparation of the surface 202 may not be required. In one aspect, preparation of the surface 202 of the substrate is not required. If the surface includes paint and the like, the paint may be chemically and/or mechanically abraded. This U It is an advantage of various examples of the present disclosure that some oxidation may be present on the surface. It is another advantage of various examples that the surface may be oxidized or anodized prior to application and this oxidation or anodized applied composition will not adversely affect subsequent application steps of the present disclosure.

If the surface 202 includes oils or other such contaminants, contact with the presently disclosed composition is performed and is sufficient to remove the contaminants to an acceptable level. The step of contacting the presently disclosed composition to the surface 202 of the substrate may be repeated until the contaminants are brought to an acceptable level. For example, the surface 202 may be contacted with the composition and then wipe dry. The surface 202 can be further evaluated prior to applying the sealant. For example, a layer of water may be applied to the surface. It is an advantage of various examples that the surface 202 may be oxidized, anodized prior to application and past history of the surface 202 of the substrate will not adversely affect subsequent application steps of the present disclosure.

The composition with the included dye can be applied to the surface 202 using any viable means such as dipping, drenching, or spraying the composition. At step 120, the composition is applied to the surface 202 of the substrate. In an example, the composition with the included dye is applied to the surface 202 of the substrate. For example, the surface 202 is dipped in, drenched, brushed, rolled, or sprayed with the composition. In a particular example, a user or operator sprays the composition on the surface 202 with a suitable spray gun. Suitable examples of spray guns include high volume low pressure (HVLP) systems, high pressure low volume (HPLV) systems, electrostatic systems, and the like. In another example, a robotically controlled applicator nozzle is controlled to apply the composition to the surface 202 of the substrate. In one aspect, the composition can be clear, transparent, or translucent and formulated to include the dye.

After application of the composition, the composition is allowed to air dry for a predetermined amount of time and/or until a predetermined surface characteristic is achieved such as, the surface 202 is dry to the touch, or displays the characteristic: of the dye, or the like.

The composition after application is optionally evaluated. In various examples, the composition is not evaluated following application, but rather, at the time of application. Alternatively, a post-application inspection is performed to verify appropriate application dye on the surface 202 of the substrate.

As indicated in block 115, the process of applying the composition to the surface is exemplified. In an example, the surface is dipped in, drenched, or sprayed with the composition. More generally, any suitable composition that includes the dye may benefit from various examples of the present disclosure.

At step 120, the composition with the included dye is applied to the surface which may be optionally prepared to receive the composition. For example, the surface is dipped in, drenched, brushed, rolled, wiped, or sprayed with the composition. In a particular example, a user or operator sprays the composition on the surface with a suitable spray gun. Suitable examples of spray guns include high volume low pressure (HVLP) systems, high pressure low volume (HPLV) systems, electrostatic systems, and the like. In another example, a robotically controlled applicator nozzle is controlled to apply the applied composition to the surface. Excess composition can optionally be wiped off as in step 130

At step 125 the distribution of the dye on the surface is inspected. For example, the user observes the color of the dye about the surface. In an example, the dye is controlled to generate a visible color. For example, a dye configured to have a visible appearance of color or to fluoresce in response to exposure to light of a suitable wavelength of electromagnetic radiation to fluoresce at a visible wavelength. In other examples, the dye is visible in other wavelengths of light such as white light.

At step 135, it is determined if a sufficient amount of the dye is distributed appropriately. It is an advantage of various examples that the distribution of any suitable composition be determined after applying the composition. In response to observing one or more areas being essentially devoid of the dye or such areas being below a predetermined dye distribution, it can be determined that an insufficient amount of the dye is present and, therefore, more of the composition is applied at step 120. In response to the dye intensity or color being substantially uniformly distributed upon the surface, it is determined if an excess of the dye is present at step 140. For example, a squeegee (not necessarily to remove solvents) or absorbent cloth is utilized to remove any excess applied composition. In another example, a stream of air from an air gun or air knife is utilized to remove any excess applied composition.

At step 140, it is determined if an excess of the dye is present upon the surface or the surface has a uneven distribution of dye. For example, the prepared surface is inspected for runs and/or pooling of the dye, portions of the surface are wiped as in step 130. If the surface does not contain the same distribution or any dye, the composition application step 120 can be repeated. Specifically, relatively low points, creases, areas in reduced lighting conditions, or other such surface characteristics are inspected. In response to an excess of the dye being present upon the surface, the excess is removed at step 130. In response to one or more area being essentially devoid of the dye or below a predetermined distribution, color or color intensity, it may be determined that an insufficient amount of cleaning out the surface 202 of the substrate has been performed, and, therefore, more of the composition is applied or repeated. In response to determining that an excess of the dye is not present upon the surface and a uniform distribution of dye is present on the surface, a sealant can be applied to the surface as in step 145.

At step 145, after sealant is applied and the surface is put into service for a time interval or "post-application sealant inspection process" as in block 155, it is determined at step 160 if the dye is substantially distributed on the surface and/or that sufficient amounts of the dye are present beneath the sealant. In response to one or more areas being essentially devoid of the dye or below a predetermined distribution as in step 160, additional composition can be applied, as this would indicated, among other things, that additional sealant is needed or required.

As indicated in block 155, at step 150, the dye of the sealant-treated surface is inspected. For example, the user observes the color of the surface through the sealant. In an example, the dye is controlled to generate the visible color through the sealant regardless of the color of the sealant, or the color of the sealant and that of the dye can be arranged to provide a color different from that of the dye and sealant. In one aspect, the dye is configured to fluoresce in response to exposure to light of a suitable wavelength of electromagnetic radiation to fluoresce at a visible wavelength. In some aspects, the dye is visible in other wavelengths of light such as white light. In some aspects, the dye is visible in the visible wavelengths of light when exposed to UV light.

In one aspect, if performed, the color imparted by the dye is removed or changes with time, for example, by chemically altering the dye to reduce its visibility or by diffusing the dye from the surface 202 of the substrate, or by normal use of the surface.

In an example, the color or intensity of color is dependent upon a thickness of the applied composition or the initial concentration of the dye in the composition. Thus, based on the color or intensity of color, the relative amount and/or distribution of the dye on the surface 202 of the substrate can be determined. It is an advantage of various examples that the amount and/or distribution of the dye of any suitable composition may be determined. Alternatively, it can be determined if a sufficient amount of the dye is present on the surface 202 of the substrate as an indication of sealant integrity.

Examples of suitable sealants include any otherwise transparent or translucent coatings, varnish, shellac, and the like. In one aspect, sealants typically employed after carrying out the present method of block 115 include, without limitation, polysulfides, polythioethers, polysilicones, polysiloxanes, and polyurethanes.

In one example, any dye color present on the surface is modified from the application of the sealant or the repeated use of the substrate in service. In various examples, the color can be removed, reduced, or otherwise altered, by UV breakdown of the dye, heating of the dye, chemically altering of the dye, and/or leaching the dye from the substrate. That is, in a particular example, the dye is configured to bleach or otherwise revert to the appearance of the surface to an essentially uncolored state after a predetermined number of uses, for example, corresponding to a known sealant responsiveness to various conditions (e.g., environmental exposures, such as a predetermined number of flights above a predetermined height).

In one aspect, a combination of different dyes are used, each with a specific function. For example, an aluminum or titanium surface contacted with the composition containing a first dye, Methyl Blue for example, which induces a pH based change in the Methyl Blue colorant, and a second dye which is completely inert to the aluminum or titanium surface. Thus, by utilizing Methyl Blue as the first dye, a strong blue color is observed during application of the composition which facilitates determining the distribution of the applied composition and dye on the surface 202 of the substrate and, thereafter, the dye is controlled to fade to a lighter color revealing only the color of the second dye. In yet other examples, colorants that are unstable when exposed to heat, extreme cold, and/or intense UV radiation are utilized as the dye and appropriate conditions to render the dye colorless are used in the composition.

It can be determined if the color has been sufficiently modified. For example, the user or operator may visually inspect the surface to determine if color remains, has changed to another color, or has been bleached. In particular, depending upon the method of color modification, areas calling for increased diligence may include those areas susceptible to shadows, crevices, and the like. In some aspects, a colorimeter is used to determine a quantifiable amount of dye color present on the surface or distributed on the surface.

Solvents suitable for use in the present method include, without limitation, methyl n-propyl ketone (MPK), methyl ethyl ketone (MEK), isopropyl alcohol (IPA), Acetone, Diestone DLS (Socomore S.A.S., Vannes, France; a mixture of monopropylene glycol methyl ether, 2-methoxy 1-methylethyl acetate, and $C_{9-11}$ n-alkanes, isoalkanes, cyclics and <2% aromatics)

Adhesion Promoters suitable for use in the present methods include without limitation transition metal alkoxide/akylalkoxide, epoxy- or mercapto silane moieties. In one aspect, the transitional metal compound is selected from one or more of the group consisting of a transitional metal alkoxide, transitional metal halo-alkoxide or a condensed transitional metal alkoxide and may comprise a mixture of these compounds. In one aspect, the transitional metal is zirconium, hafnium, titanium, and germanium alkoxide/alkylalkoxide compounds of mono-, di-, tri-, or tetra-alkoxides.

Titanium compounds include titanium alkoxides having a general formula Ti(OR)4 in which R is an alkyl group, preferably having from 1 to 8 carbon atoms. Each R group may be the same as or different from the other R groups. Suitable transitional metal alkoxides include tetra-isopropoxy titanium (tetraisopropyl titanate), tetra-n-butoxy titanium (tetra n-butyl titanate) and tetraethoxy titanium (tetraethyl titanate). Zirconium alkoxides such as zirconium n-propoxide may also be used.

The condensed alkoxides are typically prepared by careful hydrolysis of titanium alkoxides and may be represented by the formula RO[Ti(OR)$_2$O]R in which each R, independently, represents an alkyl group. Preferably, n is less than 20 and more preferably is less than 10. Preferably R contains 1 to 6 carbon atoms and useful condensed alkoxides include the compounds known as polybutyl titanate and polyisopropyl titanate.

The silane or siloxane can be one or more of (3-glycidoxypropyl)trimethoxysilane, 3-glycidoxypropyltriethoxysilane, paminophenylsilane, allyltrimethoxysilane, n-(2-aminoethyl)-3-aminopropyltrimethoxysilane, 3-aminopropyltriethoxysilane, 3-aminopropyltrimethoxysilane, 3-glycidoxypropyldiisopropylethoxysilane, (3-glycidoxypropyl)methyldiethoxysilane, 3-mercaptopropyltrimethoxysilane, 3-mercaptopropyltriethoxysilane, 3-methacryloxypropylmethyldiethoxysilane, 3-methacryloxypropylmethyldimethoxysilane, 3-methacryloxypropyltrimethoxysilane, n-phenylaminopropyltrimethoxysilane, vinylmethyldiethoxysilane, vinyltriethoxysilane, vinyltrimethoxysilane, tetraethylorthosilicate.

In one aspect, dyes suitable for use in the present methods and compositions include without limitation Fluorescein, Rose Bengal, Erythrosine B, Allura Red, Indigotine, Fast Green.

A typical formulation of the fortified cleaner involves about 99% solvent, 0.01-1% vol/vol adhesion promoter active ingredient (Titanium complexes or siloxanes) and 0.01-0.05% wt/vol of an optical dye.

While not intending to be bound by theory, it is believed that, at least in some examples, methods in accordance with the present disclosure operate by at least one of helping to ensure that the substrate surface is clean (free of contaminants); and/or helping to remove loose components of the pre-existing coating, e.g., paint and/or swelling the pre-existing coating.

Furthermore, and not intending to be bound by theory, methods in accordance with the present disclosure use a present composition including an adhesion promoter that may adhesion-activate a previously applied sealant by providing a chemical "bridge" between reactive sites on the fresh coating of sealant and reactive sites on the previously applied sealant and/or the dye.

Without being bound by theory, at least in some examples, cleaning with the solvent may remove at least a portion of surface oxidation exposing more reactive sites for the adhesion promoter to bond to. Moreover, while the coating is swollen with solvent, adhesion promoter that has already bonded on one end to the fresh coating's reactive sites may locate itself inside the pores of the coating. Mechanical interlocking may occur between the substrate and sealant when chains of the promoter become entangled with the sealant. After the solvent evaporates, these entanglements may tighten as the system shrinks.

Figure 2:
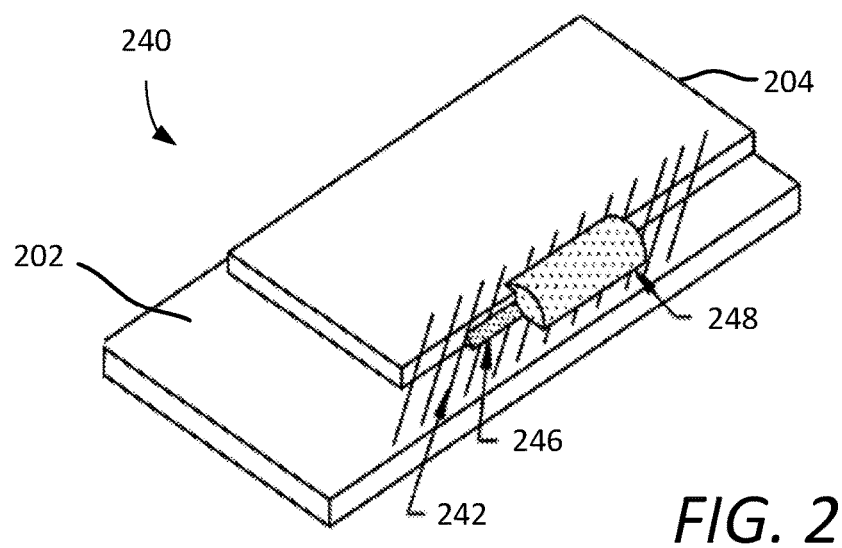
FIG. 2 is top elevation view of a conventional two-piece substrate with sealant.

FIG. 2 represents a joining of two substrates using a conventional sealant application process, where a first substrate 202 is joined to a second substrate 204 using fortified solvent application 242, a first sealant application 246, followed by a second sealant application 248.

Figure 3:
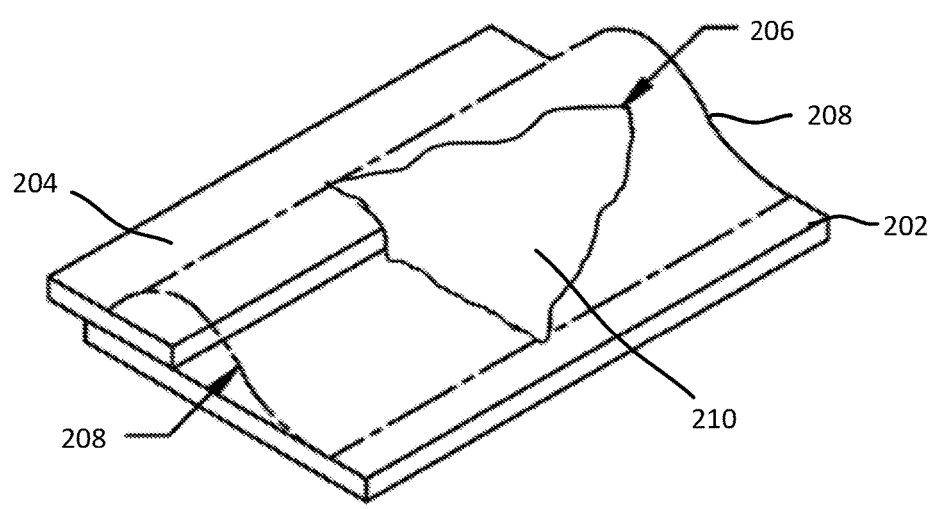
FIG. 3 is top elevation view of a two-piece substrate with sealant after use.
Figure 4:
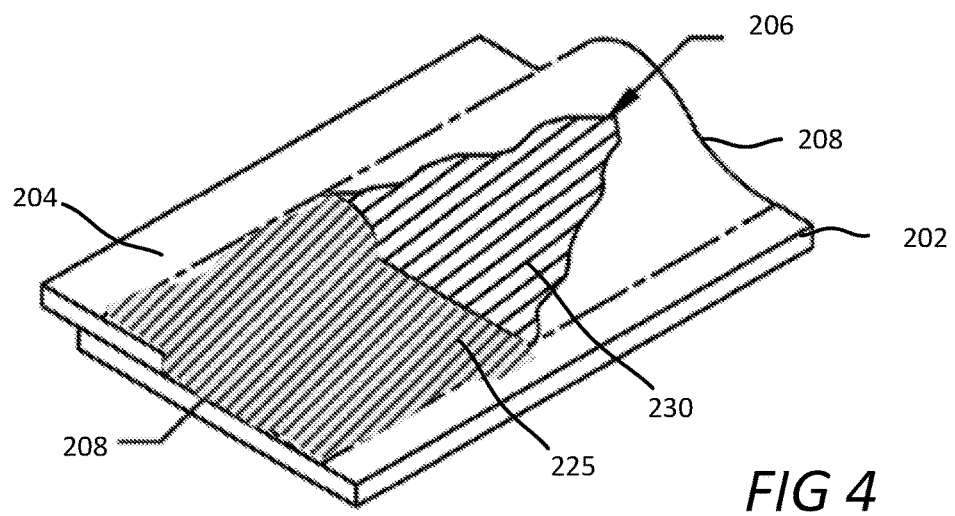
FIG. 4 is top elevation view of the two-piece substrate with sealant of FIG. 2 after treatment with the present composition used in accordance with the method of FIG. 1.

As shown in FIGS. 3, and 4, an advantage of the present disclosure it shown providing for improved rework 206 of a previously applied sealant 208 on substrate 202 overlapping a second substrate 204, where cutaway 210 is contacted with the present composition to provide sealant 225 and 230.

Figure 5:
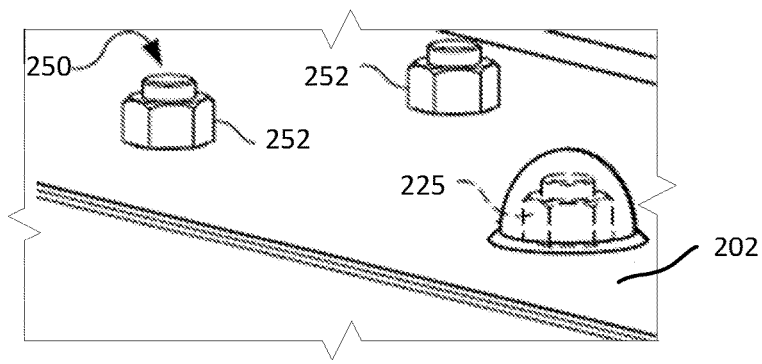
FIG. 5 is top elevation view of a substrate with fasteners treated with the present composition used in the method of FIG. 1.

As shown in FIG. 5, the present disclosure provides for contacting surface 202 having fasteners such as lug nuts 252, with the present composition 250 and subsequently with sealant 225.

Figure 6:
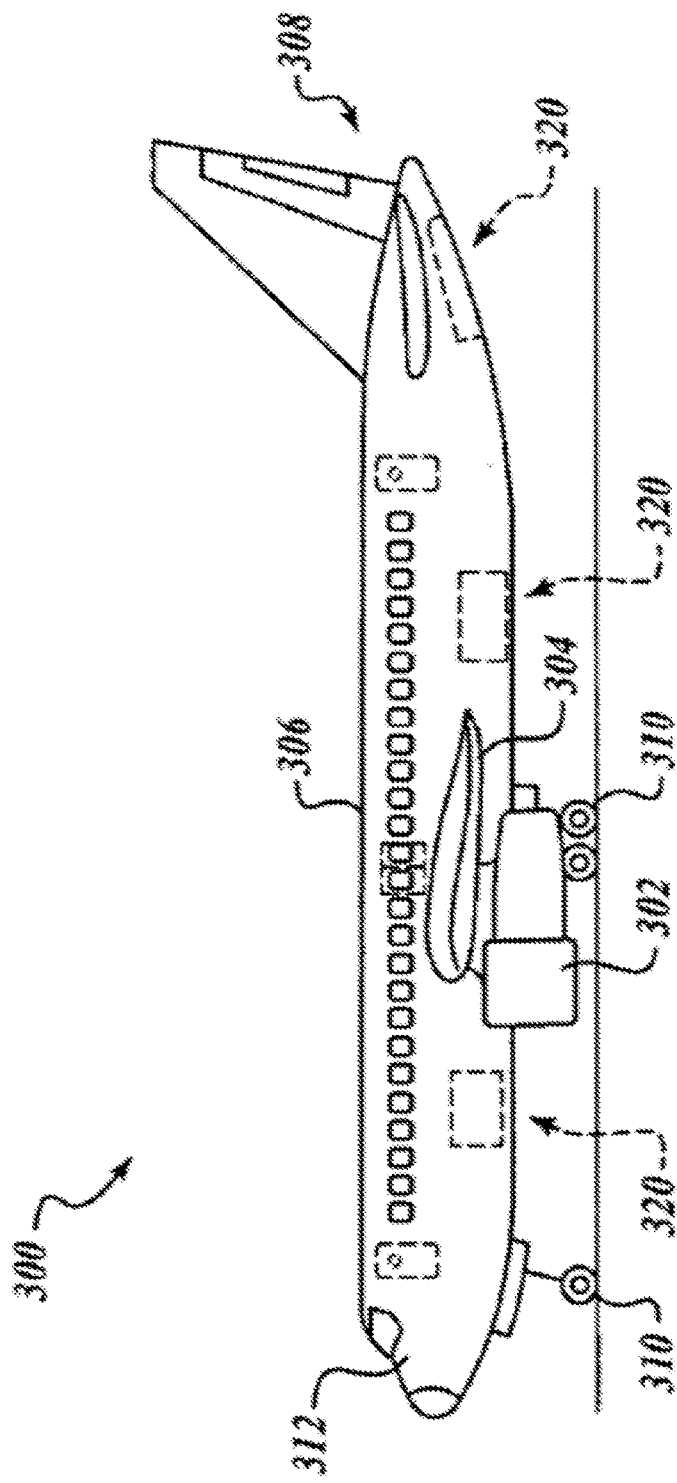
FIG. 6 is a side elevation view of an aircraft having one or more components treated using a method in accordance with an example of the present disclosure.

After reading this specification, those skilled in the art will readily recognize that examples of the present disclosure may be used to treat surfaces of a wide variety of components incorporated into a wide variety of different systems. For example, FIG. 6 shows a side elevation view of an aircraft 300 having one or more components 320 treated using methods in accordance with the present disclosure. The aircraft 300 generally includes one or more propulsion units 302 that are coupled to wing assemblies 304, or alternately, to a fuselage 306 or even other portions of the aircraft 300. Additionally, the aircraft 300 also includes a tail assembly 308 and a landing assembly 310 coupled to the fuselage 306. The aircraft 300 further includes other systems and subsystems generally required for the proper operation of the aircraft 300. For example, the aircraft 300 includes a flight control system 312 (not shown), as well as a plurality of other electrical, mechanical and electromechanical systems that cooperatively perform a variety of tasks necessary for the operation of the aircraft 300. Each of the wing assemblies 304, the fuselage 306, the propulsion unit 302, the wheels 310, and the tail 308 may include components, such as an outer skin which may desire a sealant.

Although the aircraft 300 shown in FIG. 6 generally shows a commercial passenger aircraft, it should be understood that a wide variety of components of flight vehicles of other types may be treated using methods in accordance with the present disclosure. Examples of such flight vehicles may include manned or unmanned military aircraft, rotary wing aircraft, aerospace vehicles, missiles, or ballistic flight vehicles. Further, alternative examples of the present disclosure may include exterior and interior components of a given commercial passenger aircraft.

Experimental Data

A first exemplary composition, FCS-TiB, summarized in Table 1, was prepared as follows: to a solution of MPK (300 mL), Rose Bengal dye (60 mg) was added and stirred for 30 minutes in a closed container. To this solution was added titanium(IV) butoxide (0.3 mL) and mixed thoroughly.

A second exemplary composition, FCS-TiH, summarized in Table 2, was prepared as follows: to a solution of methyl n-propyl ketone (MPK) (300 mL), Rose Bengal dye (60 mg) was added and stirred for 30 minutes in a closed container. To this solution was added Titanium(IV) 2-ethylhexyloxide (0.3 mL) and mixed thoroughly.

A third exemplary composition, FCS-TiA, summarized in Table 3, was prepared as follows: to a solution of MPK (300 mL), Rose Bengal dye (60 mg) was added and stirred for 30 minutes in a closed container. To this solution was added Titanium(IV) 2-ethylhexanoate (0.3 mL) and mixed thoroughly.

A fourth exemplary composition, FCS-GLYMO, summarized in Table 4, was prepared as follows: to a solution of MPK (300 mL), Rose Bengal dye (60 mg) was added and stirred for 30 minutes in a closed container. To this solution was added DYNASYLAN© GLYMO (Evonik, Essen, Germany) (3-glycidoxypropyltrimethoxysilane) (0.3 mL) and mixed thoroughly.

A fifth exemplary composition, FCS-MTMO, summarized in Table 5, was prepared as follows: to a solution of MPK (300 mL), Rose Bengal dye (60 mg) was added and stirred for 30 minutes in a closed container. To this solution was added DYNASYLAN© MTMO (Evonik, Essen, Germany) (3-mercapto propyltrimethoxysilane) (0.3 mL) and mixed thoroughly.

Methods

An exemplary method of preparing a surface for sealing was carried out as follows. Any visible particulates, dust, loose materials, etc. were removed from test surfaces that needed to be sealed. A cleaning rag with no contaminants was then saturated with the desired cleaning composition (composition) and was used to wipe off the substrate once ("wet wipe"). This was followed by wiping with a dry rag ("dry wipe"). This alternate cycle of wet and dry wipe can be repeated 2-3 times before application of sealant.

Examples of the present disclosure provide significant advantages over conventional treatments of substrates, in particular, metal substrates, in preparation of applying a fresh coat of sealant to that surface, even if previously contacted with a sealant. For example, examples of the present disclosure eliminate the administration of scuff sanding to a substrate, thereby providing an efficient and cost-effective solution to the labor and production issues related to scuff sanding. Examples of the present disclosure also present an economical single-step method of preparing a previously treated surface for the application of a new coating of sealant. Furthermore, because examples of the present disclosure are capable of being applied to a variety of metallic substrates, such examples are suitable for use in association with multiple functions.

While preferred and alternate examples of the present disclosure have been illustrated and described, as noted above, many changes can be made without departing from the spirit and scope of the present disclosure. Accordingly, the scope of the present disclosure is not limited by the disclosure of these preferred and alternate examples. Instead, the present disclosure should be determined entirely by reference to the claims that follow.

TABLE 1

Exemplary composition FCS-TiB.

| Components | Quantity | CAS# |
|---|---|---|
| MPK (BMS 11-9) | 99.88% | 107-87-9 |
| Titanium(IV) butoxide | 0.1% (v/v) | 5593-70-4 |
| Rose Bengal | 0.02% (wt/v) | 632-69-9 |

TABLE 2

Exemplary composition FCS-TiH.

| Components | Quantity | CAS# |
|---|---|---|
| MPK (BMS 11-9) | 99.88% | 107-87-9 |
| Titanium(IV) 2-ethylhexyloxide | 0.1% (v/v) | 1070-10-6 |
| Rose Bengal | 0.02% (wt/v) | 632-69-9 |

TABLE 3

Exemplary composition FCS-TiA.

| Components | Quantity | CAS# |
|---|---|---|
| MPK (BMS 11-9) | 99.88% | 107-87-9 |
| Titanium(IV) 2-ethylhexanoate | 0.1% (v/v) | 3645-34-9 |
| Rose Bengal | 0.02% (wt/v) | 632-69-9 |

TABLE 4

Exemplary composition FCS-GLYMO.

| Components | Quantity | CAS# |
|---|---|---|
| MPK (BMS 11-9) | 99.88% | 107-87-9 |
| DYNASYLAN GLYMO | 0.1 (v/v) | 2530-83-8 |
| Rose Bengal | 0.02% (wt/v) | 632-69-9 |

TABLE 5

Exemplary composition FCS-MTMO.

| Components | Quantity | CAS |
|---|---|---|
| MPK (BMS 11-9) | 99.88% | 107-87-9 |
| DYNASYLAN MTMO | 0.2 (v/v) | 4420-74-0 |
| Rose Bengal | 0.02% (wt/v) | 632-69-9 |

In order to investigate the enhanced adhesion/cleaning property imparted by this invention compared to conventional cleaning methods using Methyl propyl ketone, a comparative peel test study was carried out per ASTM D3330 using polysulfide-based sealants on chromic acid anodized aluminum panels. These aluminum panels were purposefully contaminated with different levels of BOE-LUBE® (a metal working lubricant, Orelube Corp., Bellport, N.Y.). They were cleaned using either MPK or FCS-TiB before the sealant was applied. These peel panels were cured for 2 weeks before peel testing using an Instron to evaluate the adhesion characteristics. The results summarized in Table 6 demonstrates that MPK cleaned panels exhibited adhesive failure (which is an indication of imperfect adhesion of the sealant to substrate).

Additional testing was performed as indicated in Table 7. Test panels of aluminum were purposefully contaminated with 1200 mg/ft.$^2$ of MICROCUT® lubricant (Prolube Lubricants, Brendale, Qld). Table 7 demonstrates that the present compositions provided excellent cleaning/adhesion properties for a conventional two-part polysulfide manganese-based sealant without brushcoat, compared to MPK solvent only cleaning. Additional testing corresponding to the equivalent of ASTM D2197-16 (scraping replaced by swiping with elastomeric material) also indicated acceptable sealant adhesion properties corresponding to the use of the present compositions.

TABLE 6

Cohesive failure results of exemplary compositions

| Panels | Cleaning solvent | Boelube (mg/panel) | Pound per Inch Wide | % Cohesive failure |
|---|---|---|---|---|
| Chromic acid anodized | MPK | 1.9 | 42.87 | 100 |
| | MPK | 4.5 | 44.41 | 90 (adhesion failure) |
| Aluminum | FCSFCS-TiB | 1.8 | 44.81 | 100 |
| | FCS-TiB | 5.5 | 46.55 | 100 |

TABLE 7

Cohesive failure results of exemplary compositions;

| # of panels | Composition | Cleaning Method | Pound per Inch Wide | | | % Cohesive Failure |
|---|---|---|---|---|---|---|
| 3 | Control | None | N/A | | | Complete failure |
| 3 | MPK | Solvent soak/dry wipe | 45.90 | 50.64 | 46.13 | 100 |
| 3 | MPK | Wet wipe/ flash off (2x) | 51.41 | 46.09 | 57.59 | 100 |
| 3 | FCS-10* | soak/dry wipe | 52.26 | 52.39 | 47.05 | 100 |
| 3 | FCS-10* | Wet wipe/ flash off (2x) | 48.53 | 50.01 | 49.44 | 100 |
| 3 | FCS-100** | soak/dry wipe | 48.38 | 49.50 | 50.22 | 100 |
| 3 | FCS-100** | Wet wipe/ flash off (2x) | 50.40 | 46.38 | 47.01 | 100 |

*10 ppm adhesion promoter;
**100 ppm adhesion promoter

We claim:
1. A method of improving adhesion of sealant to a surface, a method comprising the steps of:
    (i) contacting a surface with a liquid composition comprising at least one cleaning agent, at least one adhesion promoter, and at least one dye, the surface having a first surface contamination;
    (ii) transitioning at least one portion of the surface in a first surface contamination state to a second surface contamination state and simultaneously distributing the at least one dye on the surface associated with the second surface contamination state, the second surface contamination state having reduced or eliminated surface contamination, the transitioning step simultaneously cleaning and preparing the at least one portion of the surface for adhesion to or by another material;
    (iii) identifying remaining surface in the first surface contamination state after steps (i) and (ii) by a visual distribution of the at least one dye on the surface.

2. The method of claim 1, further comprising repeating steps (i) and (ii) after step (iii).

3. The method of claim 1, wherein the cleaning agent comprises at least one volatile organic solvent.

4. The method of claim 1, wherein the at least one cleaning agent comprises one or more volatile organic solvents selected from the group consisting of Methyl Ethyl Ketone (MEK), Methyl n-Propyl Ketone (MPK), Toluene, Isopropyl Alcohol (IPA), and Methyl Isobutyl Ketone (MIBK), acetone, and a mixture of: monopropylene glycol methyl ether, 2-methoxy 1-methylethyl acetate, and $C_{9-11}$ n-alkanes, isoalkanes, cyclics with less than 2 weight percent aromatics.

5. The method of claim 1, wherein the at least one adhesion promoter includes one or more of a transition metal alkoxide or a metal alkylalkoxide.

6. The method of claim 5, wherein the transition metal alkoxide or the metal alkylalkoxide is selected from mono-, di-, tri- and tetra (alkyl)alkoxides of aluminum, titanium, and zirconium.

7. The method of claim 6, wherein the transition metal alkoxide or the metal alkylalkoxide is selected from the group consisting of zirconium(IV) bis(diethyl citrato) dipropoxide; titanium(IV) (triethanolaminato)isopropoxide; titanium bis(triethanolamine)diisopropoxide; titanium(IV) butoxide polymer; titanium (IV) butoxide; titanium(IV) oxyacetylacetonate; titanium(IV) bis(ammonium lactato)dihydroxide; oxobis(2,2,6,6-tetramethyl-3,5-heptanedionato) titanium(IV); titanium(IV) diisopropoxidebis(2,2,6,6-tetramethyl-3,5-heptanedionate); titanium diisopropoxide bis (acetylacetonate); titanium(IV) tert-butoxide; titanium tetraisopropoxide; titanium tetrabutanoxide; and titanium (IV) 2-ethylhexanoate.

8. The method of claim 1, wherein the at least one adhesion promoter includes one or more of an epoxy-, or mercapto-functionalized mono-, di-, or tri-(alkyl)alkoxyl siloxane.

9. The method of claim 8, wherein the siloxane is selected from the group consisting of (3-aminopropyl)triethoxysilane; (gamma-mercaptopropyl)trimethoxysilane; 3-glycidoxypropyltrimethoxysilane; 3-mercapto propyltrimethoxysilane; and isocyanatopropyltriethoxysilane (IPS).

10. The method of claim 1, wherein the at least one dye has at least one absorption maximum between 390 nanometers and 700 nanometers.

11. The method of claim 10, wherein the at least one dye is selected from the group consisting of Fluorescein (3',6'-dihydroxyspiro[isobenzofuran-1(3H),9'-[9H]xanthen]-3-one); Rose Bengal (4,5,6,7-tetrachloro-3',6'-dihydroxy-2',4',5',7'-tetraiodo-3H-spiro[isobenzofuran-1,9'-xanthen]-3-one); Erythrosine B (2-(6-hydroxy-2,4,5,7-tetraiodo-3-oxo-xanthen-9-yl)benzoic acid); Allura Red (disodium 6-hydroxy-5-[(2-methoxy-5-methyl-4-sulfophenyl)azo]-2-naphthalenesulfonate); Indigotine (a mixture of disodium 3,3'-dioxo-[delta2,2'-biindoline]-5,5'-disulfonate, and disodium 3,3'-dioxo-[delta2,2'-biindoline]-5,7'-disulfonate); Fast Green (ethyl-[4-[[4-[ethyl-[(3-sulfophenyl)methyl]amino]phenyl]-(4-hydroxy-2-sulfophenyl)methylidene]-1-cyclohexa-2,5-dienylidene]-[(3-sulfophenyl)methyl]azanium); Basic Blue 41 ([[4-[ethyl(2-hydroxyethyl)amino]phenyl]azo]-6-methoxy-3-methylbenzothiazoliummethylsulphate); Direct Red 81 (disodium 7-benzamido-4-hydroxy-3-[[4-[(4-sulphonatophenyl)azo]phenyl]azo]naphthalene-2-sulphonate); and Methylene Blue (3,7-bis(dimethylamino)phenazathionium chloride.

12. The method of claim 1, wherein the surface is metal, metal alloy, composite, or a metal or metal alloy surface previously coated with a sealant coating.

13. The method of claim 12, further comprising contacting the metal or the metal alloy surface with a sealant.

14. The method of claim 13, further comprising contacting the metal or the metal alloy surface previously coated with a sealant coating with the same sealant or a different sealant.

* * * * *